United States Patent [19]

Peterson et al.

[11] Patent Number: 5,433,987
[45] Date of Patent: Jul. 18, 1995

[54] ABSORBENT SPUN-LACED FABRIC

[75] Inventors: Robert H. Peterson; James T. Summers, both of Hendersonville, Tenn.

[73] Assignee: E. I. Du Pont de Nemours and Company, Wilmington, Del.

[21] Appl. No.: 297,745

[22] Filed: Aug. 30, 1994

Related U.S. Application Data

[63] Continuation-in-part of Ser. No. 89,871, Jul. 9, 1993, Pat. No. 5,350,625.

[51] Int. Cl.6 .............. A43B 13/38; B32B 3/24; B32B 5/06; D04H 1/46
[52] U.S. Cl. ................. 428/137; 12/142 G; 12/146 B; 28/104; 28/105; 28/106; 28/107; 36/44; 156/148; 428/299; 428/300
[58] Field of Search ............... 28/104, 105, 106, 107; 428/299, 300, 137; 156/148; 36/44

[56] References Cited

U.S. PATENT DOCUMENTS

| 3,485,706 | 12/1969 | Evans. | |
|---|---|---|---|
| 3,485,709 | 12/1969 | Evans et al.. | |
| 4,635,385 | 1/1987 | Ogden | 36/43 |
| 4,808,467 | 2/1989 | Suskind et al. | 428/284 |
| 4,893,418 | 1/1990 | Ogden | 36/44 |
| 4,925,724 | 5/1990 | Ogden | 36/44 |
| 4,929,498 | 5/1990 | Suskind et al. | 428/288 |
| 4,931,355 | 6/1990 | Radwanski et al. | 428/283 |
| 5,093,190 | 3/1992 | Kwok et al. | 428/288 |
| 5,151,320 | 9/1992 | Homonoff et al. | 428/284 |
| 5,350,625 | 9/1994 | Peterson et al. | 428/219 |

Primary Examiner—James C. Cannon

[57] ABSTRACT

This invention relates to a spun-laced fabric having improved water absorbency containing a blend of certain hydrophilic cellulosic and pack resistant fibers with a hydrophobic fiber material layer attached to one side of the blend. The fabric may be used as an absorbent layer in a multilayer or laminated structure.

17 Claims, 1 Drawing Sheet

ABSORBENT SPUN-LACED FABRIC

RELATED APPLICATIONS

The present patent application is a continuation-in-part of U.S. Ser. No. 08/089,871, filed Jul. 9, 1993, now U.S. Pat. No. 5,350,625.

FIELD OF THE INVENTION

This invention relates to moisture-absorbent spun-laced fabrics and especially to spunlaced fabrics for use in materials and apparel in contact with the body to absorb perspiration and other body fluids and collect or disperse the same away from the body for the comfort or hygiene of wearers.

BACKGROUND OF THE INVENTION

As a human perspires, the perspiration preferably evaporates to cool the skin by evaporative cooling. However, as is well known, many materials that come in contact with the body prevent moisture from freely accessing the atmosphere and evaporating. To many people, the attribute of conveying moisture away from the skin is referred to when describing whether or not a fabric "breaths". Clearly, this is a well known attribute and one in which much effort has been placed to acquire.

However, there are many situations where garments or materials must also be water proof or possess some other important attribute which is opposite to the kind of open structure one envisions when thinking of a material that "breaths". For example, gloves and boots are often required to be impervious to liquids. In addition, boots and shoes are normally relatively closed structures for durability. These apparel articles are most notorious for not being able to breath.

In the above referenced patent application, a material comprised of a combination of two different types of fibrous materials was described for use in bed pads. The material has proven to be highly wickable carrying substantial amounts of fluid away from the patient. One important characteristic of the foregoing described fabric is its exceptional ability to transport moisture laterally through the pad. In trying to apply the material in the foregoing patent application to other uses, several unforeseen shortcomings have been found.

A first unforeseen problem relates to the desirability to utilize the fabric in a bonded structure such as a laminated article. In one arrangement, it was desired to bond the fabric to polyurethane foam. However, the polyurethane was wicked into the interstices of the fabric and rendered the lateral transport of moisture totally ineffective. In essence, the fabric's virtue caused this problem.

A second problem was encountered when the fabric was bonded to laminate materials on both sides to form a sandwich around the fabric. The fabric has pretty good strength to hold up to repeated washings and other abuse; however, there is a limit to its strength. It was found that the laminated structure was prone to delamination within the fabric. Essentially, the fabric becomes disentangled and this weakness in the structure of the fabric becomes most apparent when the laminated layers are rather cohesive such as a plastic film. In this arrangement, one can peel apart the laminated structure leaving part of the fabric bonded to one laminate material and the other part of the fabric bonded to the other laminate. The same general problem of the laminated structure is that is similarly susceptible to shear forces along the fabric boundary. As a shoe insert, the laminate could very well be subjected to substantial shear forces along the boundary layer.

Clearly, these problems are going to limit the usefulness of a fabric that has some very good moisture handling properties. Accordingly, it is an object of the present invention to develop a fabric design that will provide the positive attributes of the spunlaced fabric but which overcomes the drawbacks and problems as described above. It is a more particular object of the present invention to provide an improved, more robust fabric design that is suited for bonding to other materials while retaining the moisture absorbency and lateral conduction of moisture.

SUMMARY OF THE INVENTION

The objects of the invention are achieved by the provision of a two layer fabric comprising a first layer having a mixture of pack resistant fibers and cellulosic fibers and a second layer comprising hydrophobic fibers. The first layer consists essentially of about 25 to less than 50 percent, by weight, of pack resistant fibers having a dpf of about 0.75 to about 3.0 and a length from about 0.75 to about 3.0 inches, and about 75 to greater than 50 percent of crimped, synthetic, hydrophilic cellulosic fibers having a dpf of about 0.75 to about 3.0 and a length from about 0.75 to about 3.0 inches. The first and second layers are attached by needling one to the other.

BRIEF DESCRIPTION OF THE DRAWINGS

Some of the objects of the invention have now been stated and others may become apparent as the description of the invention proceeds. The invention may be more easily understood by reference to the accompanying drawing in which.

DETAILED DESCRIPTION OF THE PREFERRED EMBODIMENT

Figure 1:
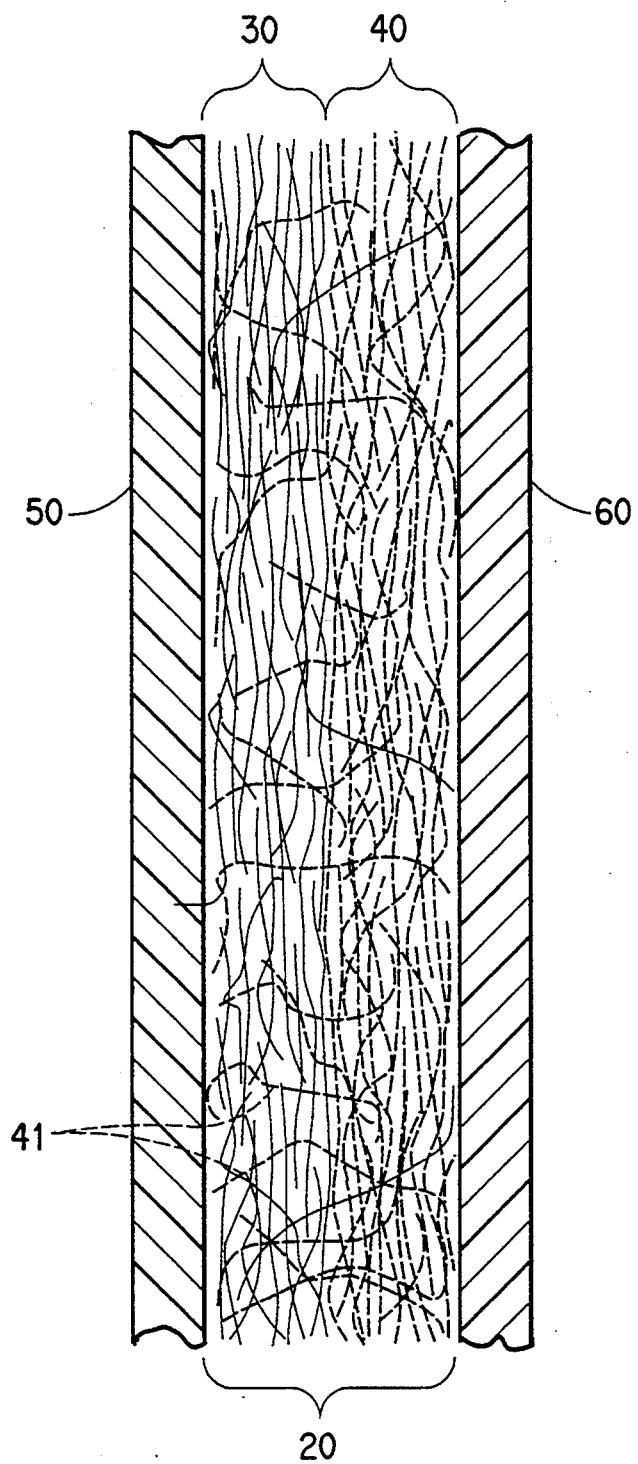
FIG. 1 is a cross sectional view of the two layer fabric which represents a preferred embodiment of the invention and which is bonded to materials at opposite faces of the fabric.

Turning now to FIG. 1, there is illustrated a cross sectional view of a laminated product, generally indicated by the number 10, which is intended to be representative of laminated products incorporating the fabric of the present invention. The laminated product 10, as illustrated comprises a fabric 20 sandwiched between lamination materials 50 and 60. The fabric 20 and lamination materials 50 and 60 may be attached by any known and conventional means, such as by adhesive or thermal bonding. The materials 50 and 60 may be any of a great variety of materials, as the particular identity of the laminates really do not form a part of this invention.

The invention primarily relates to the fabric 20, which is comprised of two layers 30 and 40. The first layer 30 is comprised of fibers (generally indicated in the drawings as solid lines) interlaced together to form a relatively open structure for the absorption and transport of fluid. This first layer 30 was described in more detail as a fabric in the parent application to the present invention and accordingly, the parent patent application Ser. No. 08/089,871 is hereby incorporated by reference herein. In the present invention, the first layer 30 is comprised of a mixture of two types of fiber. The first type of fiber is provided to maintain the openness and loft of the structure. This may also be characterized a pack resistant fiber because it resists collapsing and packing down, even when wet. Preferably, this is an acrylic spun fiber although cellulose acetate fibers, polypropylene fibers and other fibers may be suitable. The preferred acrylic fibers of this invention are comprised of polymers and copolymers of polyacrylonitrile, such as available commercially under the trademarks such as "Creslan" and "Acrilan". It is preferred that the acrylic fibers in the absorbent fabric contain a biocide, for example, one commercially known as "Microban", which can be introduced in the acrylic polymer solution during spinning. Biocide-containing acrylic fibers are commercially available. As compared with a biocide treatment that is applied topically to the already spun fibers, the "spun in" biocide tends to be considerably more permanent in effectiveness.

In conjunction with the acrylic fiber, a second type of fiber is provided for exceptional absorption of moisture. Preferably, this is a cellulosic fiber which can be any hydrophilic, cellulose-based fiber such as viscose rayon but is preferably a solvent spun cellulose such as "Lyocel" sold by Courtaulds Corporation. The amount of fiber and the deniers thereof would be selected based on the particular application of the fabric and the performance characteristics desired therefrom.

The two types of fiber are intermixed throughout the first layer 30 and the first layer is preferably consolidated by hydroentangling to form a discernible fabric like layer. A second layer 40 is thereafter added to the first layer 30. The second layer 40 is also preferably comprised of fibers (generally indicated in the drawings as dashed lines) interlaced together. The fibers in the second layer 40 preferably provide some measure of impermeability but also tend to give the fabric added strength as will be described below. Polyester fibers are preferred as they are relatively inexpensive and nonabsorbent. The fiber layers 30 and 40 are mechanically attached to one another by needling the fibers into one another. This is done preferably by hydroentangling as described in U.S. Pat. No. 3,485,706, which is also incorporated by reference herein. In accordance with the preferred embodiment of the present invention, the fibers in the first layer 30 are more lightly needled into the second layer 40 as compared with the depth to which some of the fibers of the second layer 40 are driven into the first layer 30.

By strongly needling the polyester fibers into the first layer 30, a number of individual fibers 41 extend through the first layer 30. The result of pushing the fibers of one layer extending through to the other side of the other layer may be more specifically described as "stapling" the fibers of the second layer 40 into the first layer. Thus, when a material is bonded to the first layer side of the fabric, as is layer 50, the fibers 41 are directly bonded to the first layer. Owing to the strength of polyester fibers and their ability to form strong bonds, the fibers 41 which are needled through the first layer 30 tend to lock the fabric to the material in layer 50. The polyester fibers in the second layer are also able to strongly bond to the second layer 60. As a result, the composite structure 10 is quite resistant to delamination or peeling apart of the product at the fabric 20, due to the strong polyester fibers 41 extending through both sides of the fabric 20.

In one particular aspect of the preferred embodiment of the present invention, the fibers in the second layer 40 are loosely entangled when first consolidated. The permits the fibers to be more easily driven (or needled) into the first layer 30. Also, as noted above, the needling is primarily focused on the fibers of the second layer 40 being needled into the first layer. This may be accomplished by providing more jets or higher water pressure on the second layer side of the fabric 20. As a result, few moisture absorbent and wicking fibers extend through the impermeable side of the fabric 20 and the fabric 20 tends not to absorb much moisture from the second layer side thereof as compared to the first layer side.

As discussed above, the fabric 20 of the present invention may eventually have many uses, but is presently considered to be useful in shoe liners or inserts. Several patents related to shoe inserts are U.S. Pat. Nos. 4,635,385, 4,893,418, and 4,925,724. The fabric of the present invention overcomes the drawbacks in the shoe liner art by providing lateral moisture transport. This means that when a porous material is laminated onto the first layer side of the fabric 20, the fabric will absorb it and carry it laterally within the fabric. The porous surface would then be positioned toward the wearer so as to carry away moisture from the foot. The second layer side may be provided with a polyurethane or other foam backing to provide cushioning and comfort for the wearer. However, as discussed above, the polyurethane is substantially prevented from filling and plugging the interstices of the first fabric layer 30 which the fabric 20 uses to carry the moisture laterally. Clearly, the fabric 20 provides an improvement over prior art fabrics.

EXAMPLE

An example of the fabric of this invention was assembled which comprised two webs or layers of fibers. The first layer of fibers comprised a blend of 35% by weight of Biokryl acrylic fibers and 65% Tencel cellulosic fibers. The Biokryl acrylic fibers included the antimicrobial additive, Microban, of about 0.5% by weight and may further be specified as being 3.3 decitex, 25.4 mm long, and crimped. The Tencel fibers were solvent-spun, unmodified cellulosic fibers having a substantially round cross section, 1.7 decitex and about 25.4 mm long. The blend was formed into the first web and hydroentangled in the manner generally as taught in U.S. Pat. No. 3,485,709 to Evans using a water jet profile described in the first column of Table I. The resulting fabric was stable against disentaglement and had a basis weight of 68 grams per square meter (gsm). The characteristics of the blend fabric is as set forth in the first column of Table II.

A second web was formed of 100% crimped polyester fiber of 1.5 decitex and 22 mm long. The second web was lightly consolidated by hydroentangling so as to provide a relatively stable sheet. The first and second webs were then overlaid so that the first web overlies the second web. The two webs are then needled together such that it is first subjected to hydroentangling jets from the first web side of the fabric. These jets lightly entangle the fibers. The second set of jets are arranged to impact the second web with a more vigorous entangling web and drive many of the fibers in the second web into the first web. The water jet profile is set forth in more specific detail in the second column in FIG. I.

Thereafter, samples of the fabric were provided with a laminate plastic layer of the first side of the web and a foam coating on the second side for testing as a shoe insert. By manual testing, it was found that it was very difficult to tear the composite structure apart at the fabric layer. It was also found that the foam coating did not severely penetrate through the second web of the fabric into the first web. Therefore, the lateral transport of moisture through the cellulosic layer was not substantially impaired.

TABLE I

Jet Profiles For Tencel/Biokryl//PET Blend

| Item | Tencel/Biokryl Blend | | | (Tencel/Biokryl)/ PET Laminate | | |
|---|---|---|---|---|---|---|
| | Dia. Mils | Holes/ Inch | Press. Lbs. | Dia. Mils | Holes/ Inch | Press. Lbs. |
| Cons. 1 | 7 | 10 | 150 | 5 | 40 | 300 |
| Cons. 2 | 5 | 40 | 500 | 5 | 40 | 500 |
| Belt 1 | 5 | 40 | 200 | 5 | 40 | 100 |
| Belt 2 | 5 | 40 | 600 | 5 | 40 | 300 |
| Belt 3 | 5 | 40 | 1200 | 5 | 40 | 700 |
| Belt 4 | 5 | 40 | 1800 | 5 | 20 | 1600 |
| Belt 5 | 7 | 10 | 1300 | 5 | 40 | 0 |
| Belt 6 | 7 | 10 | 1200 | 5 | 20 | 1600 |
| Drum 1 | 5 | 40 | 400 | 5 | 40 | 300 |
| Drum 2 | 5 | 40 | 1200 | 5 | 40 | 700 |
| Drum 3 | 5 | 40 | 1800 | 7 | 10 | 1800 |
| Drum 4 | 5 | 40 | 0 | 5 | 20 | 1600 |
| Drum 5 | 7 | 10 | 1000 | 7 | 10 | 1800 |
| Drum 6 | 7 | 10 | 1000 | 5 | 40 | 1200 |

The example fabric was subjected to numerous tests which are described below. The performance of the fabrics under the tests is set forth in Table II below.

TABLE II

Tencel/Biokryl//PET Blend

| Item | Tencel/Biokryl Blend | (Tencel/Biokryl)/ PET Laminate |
|---|---|---|
| Basis Wt., Oz/Yd$^2$ | 2.04 | 4.39 |
| Thickness, Mils | 31.8 | 45.2 |
| MD Grab, Lbs. | 34.7 | 97.5 |
| MD Elong., % | 36.1 | 36.1 |
| XD Grab, Lbs. | 24.7 | 60.7 |
| XD Elong., % | 65.2 | 83.2 |
| Wet MD Grab, Lbs. | 31.0 | 96.0 |
| Wet XD Grab, Lbs. | 22.3 | 57.2 |
| GAT* Absorb., % | 744 | 338 |
| GAT* T50%, Sec. | 2.9 | 5.4 |
| GAT* Rate, G/G/S | 1.33 | 0.32 |
| Wick Rate, Sec./In. | 3.4 | 3.5 |
| Intrinsic Absorb., % | 980 | 588 |
| % Tencel, app. % | 65 | 30.5 |
| % Biokryl, app. % | 35 | 16.5 |
| % Polyester, app. % | 0 | 53 |

*GAT = Gravimetric Absorbency Tester

Description of Test Methods Used

The Absorbent Capacity and Rate are measured using a Gravimetric Absorbency Tester (GATS), which is available from M&K Systems, wherein the fabric is under an approximately 350 kg per square meter load. In essence, the GATS measures the amount of liquid and rate at which it is absorbed through an orifice in the equipment.

Intrinsic absorbence is a measurement of the amount of water the fabric will absorb as a percentage of the weight of the fabric. Samples of the fabric are fully immersed in water and allowed to drain for approximately one minute. The difference in the dry and wet weight of the sample is divided by the dry weight of the sample and then multiplied by 100 so as to be expressed as a percentage.

Wick Rate is measured by the INDA STM 10.1 method.

Basis Weight, Thickness and Tensile measurements are based on ASTM D 1117 measurement methods.

The foregoing description is pertinent to an understanding of the preferred embodiment of the invention and should not be interpreted as defining or limiting the scope of the invention. The following claims set forth and define the scope of the invention.

We claim:

1. An improved spunlaced water-absorbent fabric for absorbing fluid and distributing the fluid laterally throughout the fabric, wherein the improved fabric comprises:
   a first layer having a mixture of pack resistant fibers and cellulosic fibers therein wherein the first layer consists essentially of:
      about 25 to less than 50 percent, by weight, of pack resistant fibers having a dpf of about 0.75 to about 3.0 and a length from about 0.75 to about 3.0 inches, and
      about 75 to greater than 50 percent of crimped, synthetic, hydrophilic cellulosic fibers having a dpf of about 0.75 to about 3.0 and a length from about 0.75 to about 3.0 inches; and
   a second layer comprising hydrophobic fibers wherein the first and second layers are attached by needling one to the other.

2. The fabric of claim 1 having a basis weight of from about 1.0 to 5.0 ounces per square yard.

3. The fabric of claim 1 in which the fibers in the first layer have a substantially round cross-section.

4. The fabric of claim 1 wherein the pack resistant fibers are crimped acrylic fibers.

5. The fabric of claim 4 consisting essentially of 30 to 40% acrylic fibers and correspondingly 70 to 60% solvent-spun cellulosic fibers.

6. The fabric of claim 5 wherein both types of fibers in the first layer have a dpf within the range of about 1.0 to 3.0.

7. The fabric of claim 1 wherein the pack resistant fibers in the first layer comprise cellulose acetate fibers.

8. The fabric of claim 1 wherein the pack resistant fibers in the first layer comprise polypropylene fibers.

9. The fabric of claim 1 wherein the pack resistant fibers in the first layer comprise acrylic fibers and at least some of the acrylic fibers contain an effective amount of an antimicrobial agent.

10. The fabric according to claim 9 wherein said antimicrobial agent is introduced into the acrylic polymer solution prior to spinning said acrylic fibers.

11. The fabric according to claim 1 wherein said second layer provides resistance against liquids migrating therethrough such that liquids which are outside the fabric on the second layer side thereof are generally restricted from entering the first layer of the fabric.

12. The fabric according to claim 1 wherein a portion of the ends of the hydrophobic fibers of the second layer extend through the first layer for bonding to material on the first layer side of the fabric.

13. The fabric according to claim 1 wherein the said second layer is hydroentangled into the first layer.

14. The fabric of claim 1 wherein the hydrophobic fibers in the second layer comprise polyester fibers.

15. A process for making a moisture absorbing fabric having substantial moisture absorbent and wicking properties while possessing improved strength in laminated goods, the process comprising:

forming a batt of fibers wherein the batt essentially consists of about 25 to less than 50 percent, by weight, of pack resistant fibers having a dpf of about 0.75 to about 3.0 and a length from about 0.75 to about 3.0 inches, and about 75 to greater than 50 percent of crimped, synthetic, hydrophilic cellulosic fibers having a dpf of about 0.75 to about 3.0 and a length from about 0.75 to about 3.0 inches;

hydroentangling the batt to form a spunlaced moisture absorbent first layer fabric;

assembling a second fiber fabric comprising hydrophobic fibers;

hydroentangling the hydrophobic fibers together to form a cohesive polyester fiber fabric;

overlying the first layer fabric with the hydroentangled polyester fiber fabric; and needling the polyester fibers into the first layer fabric to form the two layer spunlaced fabric.

16. The process according to claim 15 wherein the step of needling the hydrophobic fibers into the first layer fiber fabric comprises stapling polyester fibers by hydroentangling into the first layer fabric.

17. The process according to claim 16 wherein the step of hydroentangling the polyester fiber fabric comprises gentler hydroentangling as compared to the hydroentangling of the polyester fibers from the polyester fiber layer into the first layer fabric to allow for less entangled polyester fibers which are easier to drive into the first layer fabric.

* * * * *